United States Patent [19]

Nogami et al.

[11] Patent Number: 4,904,588
[45] Date of Patent: Feb. 27, 1990

[54] METHOD FOR PRODUCING L-SORBOSE

[75] Inventors: Ikuo Nogami; Hideo Shirafuji, both of Nagaokakyo; Takamasa Yamaguchi, Suita; Masahide Oka, Kawanishi, all of Japan

[73] Assignee: Takeda Chemical Industries, Ltd., Osaka, Japan

[21] Appl. No.: 11,826

[22] Filed: Feb. 6, 1987

[30] Foreign Application Priority Data

Feb. 11, 1986 [JP] Japan .................................. 61-28719
Sep. 9, 1986 [JP] Japan ................................ 61-212953

[51] Int. Cl.$^4$ ..................... C12P 19/02; C12N 1/20; C12R 1/01; C12R 1/02
[52] U.S. Cl. .................................. 435/105; 435/823; 435/822; 435/252.1
[58] Field of Search ................. 435/105, 823, 84, 822, 435/253

[56] References Cited

U.S. PATENT DOCUMENTS 2,207,768  7/1940  Weijard et al. ....................... 195/49
4,421,568  12/1983  Huibers ............................... 435/823

FOREIGN PATENT DOCUMENTS 199548  10/1986  European Pat. Off. .
0199548  4/1986  United Kingdom ................ 435/105

OTHER PUBLICATIONS

*Chemical Abstracts,* "System for Continuous Microbiological Oxidation of D-Sorbitol to L-Sorbose," Oct. 22, 1984, vol. 101, #149753(j), p. 560.
Koeblin, Chemical Abstracts 87:79000c, 1977.
Nikolskaya et al., Chemical Abstracts 101:149753j, 1984.

*Primary Examiner*—Johnnie R. Brown
*Assistant Examiner*—Pamela S. Webber
*Attorney, Agent, or Firm*—Wenderoth, Lind & Ponack

[57] ABSTRACT

L-sorbose, an intermediate important in vitamin C synthesis, is produced in higher yield from D-sorbitol by microbiological oxidation using a microorganism which belongs to the genus *Gluconobacter* and which has decreased ability to grow with D-sorbitol as the single carbon source compared with that of its parent strains.

5 Claims, No Drawings

METHOD FOR PRODUCING L-SORBOSE

The present invention relates to L-sorbose-producing bacteria and a process for producing L-sorbose, specifically a production process for L-sorbose using microorganisms of the genus Gluconobacter possessing both the ability to produce L-sorbose from D-sorbitol and decreased ability to grow with D-sorbitol as the single carbon source.

The purpose of the present invention is to provide an industrially economical production process for L-sorbose, an intermediate important in vitamin C synthesis.

L-Sorbose is now produced by oxidizing D-sorbitol using microorganisms, mainly bacteria of the genus Gluconobacter. In the conventional production process for L-sorbose by fermentation, the yield of L-sorbose from D-sorbitol as the raw material exceeds 90%, but by-products such as D-fructose, 5-ketofructose, 2-keto-D-gluconic acid and low-molecular weight organic acids are produced simultaneously; it cannot be regarded as a complete method from the point of view of the yield of the desired product.

Thus, in the industrial production of vitamin C, it is very important to improve the efficiency of the conversion of D-sorbitol to L-sorbose for reducing the cost of raw material.

Under these conditions, the present inventors made many studies on the improvement of the efficiency of L-sorbose fermentation and found that bacterial strains possessing decreased ability to grow with D-sorbitol as the single carbon source, induced from Gluconobacter bacteria used conventionally for the production of L-sorbose, possess notably improved ability to convert D-sorbitol to L-sorbose thus, developing the present invention.

An object of the present invention is to provide a production process for L-sorbose characterized by the microorganisms of the genus Gluconobacter possessing decreased ability to grow with D-sorbitol as the single carbon source. Another object is to provide L-sorbose-producing microorganisms, which are used in the above production process.

Any microorganisms can be used for the production process involved in the present invention, as long as they both belong to the genus Gluconobacter and possess both L-sorbose-producing ability and decreased ability to grow with D-sorbitol as the single carbon source. Such microorganisms can be induced from L-sorbose-producing microorganisms of the genus Gluconobacter as parent strains. Examples of microbial species which can be used as such parent strains are listed below.

| Species | Strain No. | | | |
|---|---|---|---|---|
| Gluconobacter oxydans | IFO | 3189, | IFO | 12467 |
| Gluconobacter suboxydans | IFO | 3254, | IFO | 3255 |
| | IFO | 3256, | IFO | 3257 |
| | IFO | 12528 | | |
| Gluconobacter melanogenus | IFO | 3292, | IFO | 3293 |
| | IFO | 3294 | | |
| Gluconobacter albidus | IFO | 3250, | IFO | 3253 |
| Gluconobacter capsulatus | IFO | 3462 | | |
| Gluconobacter cerinus | IFO | 3263, | IFO | 3264 |
| | IFO | 3265 | | |
| Gluconobacter dioxyacetonicus | IFO | 3271, | IFO | 3274 |
| Gluconobacter gluconicus | IFO | 3285, | IFO | 3286 |
| Gluconobacter industrius | IFO | 3260 | | |
| Gluconobacter nonoxygluconicus | IFO | 3275, | IFO | 3276 |

Note:
The above strains are the known strains listed on "List of Cultures, 1984, Seventh Edition" published by Institute For Fermentation, Osaka (IFO), Japan.

The microorganisms used for the present invention can be clearly distinguished from their parent strains in that their growth is extremely slow in a minimum media in which D-sorbitol is contained as the single carbon source. It doesn't matter whether the minimum edge is liquid or solid. When a solid medium is used, the replica-plating method is convenient for distinguishing from the parent strain. When a liquid medium is used, the microorganism involved in the present invention is inoculated to a minimum medium containing D-sorbitol as the single carbon source under the same conditions as those used for its parent strain and shaking culture is conducted usually at about 30° C. for 1~3 days. The thus obtained mutant microorganism can be distinguished from its parent strain by measuring conventionally the degree of its growth in the resulting culture on the basis of either the optical absorbance, turbidity or bacterial cell weight of the culture. The microorganisms used for the present invention should exhibit growth, the degree of which is lower than that of their parent strains; it is particularly preferable that the degree of their growth be less than 1/10 of that of their parent strains.

The microorganisms used for the present invention can be easily induced and isolated by ordinary methods.

That is, the desired strains can be easily induced from their parent strains after ordinary mutagenic treatment, such as irradiation with ultraviolet, X-rays or γ-rays or treatment with a chemical mutagen such as N-methyl-N'-nitro-N-nitrosoguanidine, methylmethanesulfonic acid or nitrous acid.

Said microorganisms may possess various auxotrophies, drug-resistances, drug-sensitivities, etc. as well as the properties described above.

Microorganisms which can be used for the present invention include Gluconobacter suboxydans BL-9 (IFO 14489, FERM P-8632) and Gluconobacter suboxydans BL-115 (IFO 14490, FERM P-8631), which were induced from Gluconobacter suboxydans IFO 3254, an L-sorbose-producing bacterium, and Gluconobacter oxydans GO-10 (IFO 14537, FERM BP-1169) and Gluconobacter oxydans GO-14 (IFO 14538, FERM BP-1170), which were induced from Gluconobacter oxydans IFO 12467, another L-sorbose-producing bacterium.

The IFO numbers and FERM P numbers described above represent deposit numbers at the Institute for Fermentation, Osaka (IFO; 17-85, Juso-honmachi 2-chome, Yokogawa-ku, Osaka, Japan) and those at the Fermentation Research Institute, Agency of Industrial Science and Technology, Ministry of International Trade and Industry, Japan (FRI, Yatabemachi-higashi 1-chome, Tsukuba, Ibaraki, Japan), respectively; the FERM BP numbers represent deposit numbers under the Budapest Treaty at the FRI. Said BL-9 and BL-115 strains were deposited at the IFO on Jan. 21, 1986 and at the FRI on Feb. 1, 1986; GO-10 and GO-14 strains were deposited at the IFO on Aug. 28, 1986 and at the FRI on Sept. 5, 1986.

BL-9 and BL-115 strains deposited at FRI were converted to deposits under the Budapest Treaty on Dec.

22, 1986 as deposit Nos. FERM BP-1241 and FERM BP-1240, respectively.

The method of microbiological oxidation of D-sorbitol is now described here. Thus, D-sorbitol can be microbiologically oxidized by culturing a microorganism which belongs to the genus Gluconobacter possessing both L-sorbose-producing ability and decreased ability to grow with D-sorbitol as the single carbon source in a D-sorbitol-containing medium to accumulate in the culture liquid L-sorbose, which is then collected.

D-Sorbitol should be contained in the culture medium at a concentration of approx. 10~50%, preferably 20-50% by weight. The culture medium should be either an enriched medium or a synthetic medium and should contain at least one carbon source, at least one nitrogen source, minerals, growth factors, etc.

D-Glucose, D-fructose, D-mannitol, glycerol, ethanol, molasses, starch hydrolysate, etc. can be added as carbon sources if necessary. For example, when a microorganism which hardly grows in a medium containing D-sorbitol as the single carbon source is cultured, it is in general preferable that a carbon source be added in an amount approx. 0.1~10% by weight that of D-sorbitol. In cases where the microorganism can grow to some degree in such a minimum medium, though its ability to grow with D-sorbitol as the single carbon source is extremely weaker than that of its parent strain, a part of the raw material D-sorbitol can be utilized as a carbon source, enabling culturing without any other carbon sources.

Substances which can be used as nitrogen sources include nitrogen-containing organic substances such as corn steep liquor, yeast extract, dry yeast, defatted soybean meal, meat extract, peptone and casamino acid; inorganic nitrogen compounds such as ammonium sulfate, ammonium nitrate, ammonium chloride, ammonium phosphate and aqueous ammonia; amino acids such as sodium glutamate; urea; and ammonium acetate. Various metals, vitamins, amino acids, nucleic acids, phosphates, etc. which are essential to the growth of the microorganism used can also be added to the medium.

It is recommended that the culturing be carried out under aerobic conditions, i.e. shaking culture, submerged culture, etc. are preferably. Culturing temperature should be 15°~40° C., preferably 25°~35° C.; medium pH should be between 3.0 and 8.0, preferably between 4.0 and 6.5; culturing time should be about 10~100 hours, preferably 15~40 hours.

L-sorbose in the resulting culture obtained as described above can be purified and separated by a method already published and in the public domain. For example, the resulting culture is filtered to remove bacterial cells, decolored using activated charcoal and then concentrated under reduced pressure, after which L-sorbose is crystallized using methanol, ethanol, acetone, etc. to separate it.

Compared to conventional processes, the present invention makes it possible to increase L-sorbose yield in its production from D-sorbitol by microbiological oxidation. That is, the yield of L-sorbose from D-sorbitol obtained by conventional processes is at most 93% or so, while that with the process involved in the present invention is more than 2-3% higher; moreover, the production of by-products such as D-fructose, 2-ketogluconic acid and 5-ketofructose is reduced. Therefore, the present process supplies L-sorbose, the raw material cost of which represents a great part of the overall cost of vitanim C production, less expensively than do conventional processes. As a result, vitamin C, which is widely used for pharmaceuticals, foods, etc., can be produced at a lower cost.

The present invention is hereinafter described more concretely with some examples of its preferred embodiment.

EXAMPLE 1

*Gluconobacter suboxydans* IFO 3254 was inoculated to a test tube containing 5 ml of an SCM medium (pH 7.0) composed of 2.5% D-sorbitol, 1.0% peptone and 1.0% yeast extract and subjected to shaking culture at 30° C. overnight. 0.25 ml of the resulting culture broth was transferred to a 200-ml conical flask containing 25 ml of the same medium and subjected to shaking culture at 30° C. for 6 hours. The resulting culture liquid was centrifuged (10,000 rpm, 10 min.) and the separated cells were washed twice with 10 ml of a tris-maleate buffer solution (0.05M, pH 6.0). The washed cells were then suspended ($2 \times 10^9$ cells/ml) in 5 ml of a tris-maleate buffer solution containing 100 µg/ml N-methyl-N'-nitro-N-nitrosoguanidine and shaken at 30° C. for 30 minutes. Cells were collected from the treated solution by centrifugation and washed twice with 10 ml of a 0.85% saline solution.

The washed cells were then transferred to 5 ml of an SCM medium supplemented with 2.5% glycerol and subjected to shaking culture at 30° C. for 1 hour to promote the segregation of mutants. The resulting suspension of cells received mutagenic treatment, and were then spread over plates of a minimum medium containing glycerol (2.5%) as the single carbon source (Table 1) so that about 100 colonies would be formed per plate and cultured at 28° C. for 3 days.

The resulting colonies were then transferred by the replica-plating method to plates of a minimum medium containing 2.5% D-sorbitol as the single carbon source and of a minimum medium containing 2.5% L-sorbose as the single carbon source and cultured at 28° C. for 3 days. As a result, a large number of mutants were obtained, which grew in the minimum medium containing glycerol as the single carbon source, but which either did not grow or grew much more slowly than did the parent strain IFO 3254 in the minimum medium containing D-sorbitol as the single carbon source and/or in the minimum medium containing L-sorbose as the single carbon source.

Of these mutants, 27 were examined for L-sorbose producing ability using the same method as that in Example 2; the strains BL-9 and BL-115 were selected, both of which are conspicuously more excellent in L-sorbose producing ability than their parent strains.

TABLE 1

| Composition of Minimum Medium | |
|---|---|
| Carbon source | 25 g/l |
| *Monosodimm L—glutamate | 2 g/l |
| $KH_2PO_4$ | 0.47 g/l |
| $CaCO_3$ | 0.18 g/l |
| $MgSO_4.7H_2O$ | 0.10 g/l |
| Nicotinamide | 30 mg/l |
| Calcium pantothenate | 3 mg/l |
| p-Aminobenzoic acid | 1 mg/l |
| Vitamin $B_2$ | 1 mg/l |
| $FeSO_4.7H_2O$ | 1.5 mg/l |
| $MnSO_4.7H_2O$ | 0.1 mg/l |

TABLE 1-continued

| Composition of Minimum Medium | |
|---|---|
| Agar (for solid media) | 20 g/l |

*Note:
In general, Gluconobacter bacteria cannot grow with L—glutamic acid as the single carbon source.

Table 2 shows the comparison in the degree of growth in various minimum media containing different carbon-containing substances as single carbon sources between *Gluconobacter suboxydans* BL-9 (IFO 14489, FERM BP-1241) and *Gluconobacter suboxydans* BL-115 (IFO 14490, FERM BP-1240) and their parent strain IFO 3254. For this comparison, the following experimental conditions were used:

One drop of each of the cell suspensions of the said 3 bacterial strains were inoculated to 5 ml of each of the minimum media which have the composition shown in Table 1 and which contain one of the carbon sources (2.5%) shown in Table 2 and cultured at 30° C. for 2 days using a test tube shaker. To the resulting culture liquid was added 0.1 ml 1N hydrochloric acid to dissolve the remaining calcium carbonate, after which the degree of growth was determined on the basis of the optical absorbance (at 600 nm) of the solution.

TABLE 2

| Carbon Source | Relative Degree of Growth Strain | | |
|---|---|---|---|
| (2.5%) | BL-9 | BL-115 | IFO 3254 |
| Glycerol | 1.012 | 1.939 | 1.593 |
| D-Sorbitol | 0.010 | 0.049 | 1.584 |
| D-Mannitol | 1.895 | 2.000 | 1.266 |
| D-Fructose | 1.033 | 1.920 | 1.699 |
| L-Sorbose | 0.005 | 0.058 | 1.649 |
| D-Glucose | 0.984 | 0.840 | 0.466 |

As is clear in Table 2, the strains BL-9 and BL-115 are both conspicuously lower in the degree of growth in a medium containing D-sorbitol as the single carbon source than their parent strain IFO 3254.

EXAMPLE 2

*Gluconobacter suboxydans* BL-9 (IFO 14489, FERM BP-1241) and *Gluconobacter suboxydans* BL-115 (IFO 14490, FERM BP-1240) were used as inocula. Each strain was inoculated to a 200-ml conical flask containing 20 ml of a 1st-seed medium (pH 6.5) composed of 50 g/l D-sorbitol, 5 g/l glycerol, 2 g/l monosodium L-glutamate, 0.3 g/l yeast extract, 0.47 g/l $KH_2PO_4$, 0.1 g/l $MgSO_4.7H_2O$, 0.18 g/l $CaCO_3$, 30 mg/l nicotinamide, 3 mg/l calcium pantothenate, 1 mg/l vitamin $B_2$ 1 mg/l p-aminobenzoic acid, 1.5 mg/l $FeSO_4.7H_2O$ and 0.1 mg/l $MnSO_4.7H_2O$ and cultured at 30° C. for 24 hours. 2 ml of the resulting culture liquid were transferred to a 200 ml conical flask containing 20 ml of a 2nd-seed medium (modified the 1st medium by increasing D-sorbitol concentration to 200 g/l) and subjected to shaking culture at 30° C. for 24 hours to obtain a 2nd-seed culture liquid.

One ml of the resulting 2nd culture liquid was then transferred to a 200-ml baffled conical flask containing 20 ml of a fermentation medium (pH 6.5) composed of 300 g/l D-sorbitol, 1 g/l glycerol, 0.3 g/l yeast extract, 0.47 g/l $KH_2PO_4$, 0.1 g/l $MgSO_4.7H_2O$, 0.18 g/l $CaCO_3$, 0.29 g/l ammonium acetate, 30 mg/l nicotinamide, 3 mg/l calcium pantothenate, 1 mg/l vitamin $B_2$, 1 mg/l p-aminobenzoic acid, 1.5 mg/l, $FeSO_4.7H_2O$ and 0.1 mg/l $MnSO_4.7H_2O$ and subjected to shaking culture at 30° C. for 24 hours. The parent strain *Gluconobacter suboxydans* IFO 3254 was simultaneously cultured as the control under the same conditions. Table 3 shows the results of these culturing experiments. In all the resulting cultures, D-sorbitol was found to have been completely consumed.

TABLE 3

| | L-Sorbose Yields |
|---|---|
| Strain | Molar Yield of L-Sorbose (based on D-Sorbitol) |
| BL-9 | 97.6% |
| BL-115 | 98.8% |
| IFO 3254 | 93.4% |

The contents of D-sorbitol and L-sorbose were determined by high performance liquid chromatography (mobile phase: pH 2.2 dilute sulfuric acid; flow rate: 0.5 ml/min.; detector: differential refractometer) using columns packed with sulfonated polystyrene gel (Shimadzu Corp., SCR-101H column, 7.9 mm×30 cm).

EXAMPLE 3

*Gluconobacter suboxydans* BL-115 (IFO 14490, FERM BP-1240) as the inoculum was cultured in the same manner as that in Example 2 to obtain 2nd-seed culture.

150 ml of the resulting 2nd-seed culture liquid was then transferred to a 5-l fermentor containing 3 l of the same fermentation medium as that used in Example 2 and cultured at 30° C., 300 rpm agitation rate and 2.4 l/min. aeration rate for 24 hours.

During the cultivation, the raw material D-sorbitol was completely oxidized; L-sorbose was accumulated in the culture broth to a yield of 98.4% based on D-sorbitol. The parent strain *Gluconobacter suboxydans* IFO 3254 was simultaneously cultured under the same conditionsl L-sorbose was found to have accumulated in the culture to a yield of 93.7% based on D-sorbitol.

EXAMPLE 4

*Gluconobacter oxydans* IFO 12467 was subjected to mutagenic treatment with N-methyl-N'-nitro-N-nitrosoguanidine using the same procedure as shown in Example 1. The resulting suspension of cells was then spread over plates of the minimum medium (Table 1) containing glycerol as the single carbon source so that approx. 100 colonies would be formed per plate after incubation at 28° C. for 4 days.

The resulting colonies were transferred by the replica-plating method to plates of a minimum medium containing D-sorbitol as the single carbon source and cultured at 28° C. for 3 days. As a result, a large number of mutants were obtained, which grew in the minimum medium containing glycerol as the single carbon source, but which either did not grow or grew much more slowly than the parent strain IFO 12467 in the minimum medium containing D-sorbitol as the single carbon source.

Of these mutants, 43 were examined for L-sorbose producing ability using the same method as described in Example 5; the strains GO-10 (IFO 14537, FERM BP-1169) and GO-14 (IFO 14538, FERM BP-1170) were selected, both of which are conspicuously higher in L-sorbose producing ability than their parent strain.

Table 4 shows the comparison of the degree of growth in various minimum media containing different carbon-containing substances as single carbon sources between *Gluconobacter oxydans* GO-10 and *Gluconobacter oxydans* GO-14 and the parent strain IFO 12467. These results were obtained using the same experimental conditions as those shown in Example 1.

TABLE 4

| Carbon Source (2.5%) | Relative Degree of Growth Strain | | |
|---|---|---|---|
| | GO-10 | GO-14 | IFO 12467 |
| Glycerol | 1.148 | 1.224 | 1.033 |
| D-Sorbitol | 0.008 | 0.008 | 0.145 |
| D-Mannitol | 0.515 | 0.665 | 0.774 |
| D-Fructose | 0.039 | 0.037 | 0.049 |
| L-Sorbose | 0.006 | 0.002 | 0.010 |
| D-Glucose | 0.739 | 0.681 | 0.616 |

AS is clear in Table 4, GO-10 and GO-14 strains can hardly grow in the minimum medium containing D-sorbitol as the single carbon source. It should be noted that both the parent strain IFO 12467 as well as the selected strains GO-10 and GO-14 hardly grew in the minimum medium containing L-sorbose as the single carbon source.

EXAMPLE 5

*Gluconobacter oxydans* GO-10 (IFO 14537, FERM BP-1169) and *Gluconobacter oxydans* GO-14 (IFO 14538, FERM BP-1170) were used as inocula. Each was inoculated to a conical flask containing 20 ml of an original medium (pH 6.5) composed of 50 g/l D-sorbitol, 5 g/l glycerol, 2 g/l monosodium L-glutamate, 1 g/l yeast extract, 0.47 g/l $KH_2PO_4$, 0.1 g/l $MgSO_4 \cdot 7H_2O$, 0.18 g/l $CaCO_3$, 30 mg/l nicotinamide, 3 mg/l calcium pantothenate, 1 mg/l vitamin $B_2$, 1 mg/l p-aminobenzoic acid, 1.5 mg/l $FeSO_4 \cdot 7H_2O$ and 0.1 mg/l $MnSO_4 \cdot 7H_2O$ and subjected to shaking culture at 30° C. for 24 hours.

One ml of the resulting culture was transferred to a 200-ml conical flask containing 20 ml of a fermentation medium (modified the original medium by increasing D-sorbitol concentration to 200 g/l) and subjected to shaking culture at 30° C. for 40 hours. The parent strain *Gluconobacter oxydans* IFO 12467 was simultaneously cultured as the control using the same conditions as above. Table 5 shows the results of these culturing experiments. In the resulting culture, D-sorbitol was found to have been completely consumed.

TABLE 5

| | L-Sorbose Yields | |
|---|---|
| Strain | Molar Yield of L-Sorbose (based on D-Sorbitol) |
| GO-10 | 96.5% |
| GO-14 | 96.3% |
| IFO 12467 | 90.1% |

The contents of D-sorbitol and L-sorbose were determined by the method described in Example 2.

What we claim is:

1. A process for producing L-sorbose, which comprises oxidizing D-sorbitol microbiologically using a mutant microorganism selected from the group consisting of *Gluconobacter suboxydans* BL-9 (FERM BP-1241), *Gluconobacter suboxydans* BL-115 (FERM BP-1240), *Gluconobacter oxydans* GO-10 (FERM BP-1169) and *Gluconobacter oxydans* GO-14 (FERM BP-1170), said mutant microorganism having a degree of growth in minimum media containing D-sorbitol as the single carbon source which is less than 1/10 of said degree of growth of the parent strain of said mutant microorganism.

2. A microorganism selected from the group consisting of *Gluconobacter suboxydans* BL-9 (FERM BP-1241), *Gluconobacter suboxydans* BL-115 (FERM BP-1240), *Gluconobacter oxydans* GO-10 (FERM BP-1169) and *Gluconobacter oxydans* GO-14 (FERM BP-1170), said microorganism having a degree of growth in minimum media containing D-sorbitol as the single carbon source which is less than 1/10 of said degree of growth of the parent strain of said microorganism.

3. A biologically pure culture of a microorganism belonging to the genus Gluconobacter having characteristics identifiable with those of a member selected from the group consisting of FERM BP-1241, FERM BP-1240, FERM BP-1169 and FERM BP-1170, said culture oxidizing D-sorbitol to L-sorbose in a culture medium containing assimilable carbon and digestable nitrogen sources, said microorganism having a degree of growth in minimum media containing D-sorbitol as the single carbon source which is less than 1/10 of said degree of growth of the parent strain of said microorganism.

4. The process according to claim 1, wherein the mutant microorganism is *Gluconobacter suboxydans* BL-9 (FERM BP-1241) or *Gluconobacter suboxydans* BL-115 (FERM BP-1240).

5. The process according to claim 1, wherein the mutant microorganism is *Gluconobacter oxydans* GO-10 (FERM BP-1169) or *Gluconobacter oxydans* GO-14 (FERM BP-1170).

* * * * *